(12) United States Patent
Hisamoto et al.

(10) Patent No.: US 8,563,260 B2
(45) Date of Patent: Oct. 22, 2013

(54) CAPILLARY FOR IMMUNOASSAY, AND CAPILLARY IMMUNOASSAY METHOD USING SAME

(75) Inventors: Hideaki Hisamoto, Sakai (JP); Terence Gaba Henares, Batangas (PH)

(73) Assignee: Osaka Prefecture University Publication Corpoaration, Osaka (JP)

( * ) Notice: Subject to any disclaimer, the term of this patent is extended or adjusted under 35 U.S.C. 154(b) by 239 days.

(21) Appl. No.: 13/140,700

(22) PCT Filed: Dec. 7, 2009

(86) PCT No.: PCT/JP2009/070485
§ 371 (c)(1),
(2), (4) Date: Jun. 20, 2011

(87) PCT Pub. No.: WO2010/071045
PCT Pub. Date: Jun. 24, 2010

(65) Prior Publication Data
US 2011/0262940 A1    Oct. 27, 2011

(30) Foreign Application Priority Data
Dec. 19, 2008   (JP) .................... 2008-324059

(51) Int. Cl.
*G01N 33/53*   (2006.01)
(52) U.S. Cl.
USPC ....... 435/7.9; 435/7.1; 435/287.2; 435/288.7; 436/518; 436/532; 436/535

(58) Field of Classification Search
None
See application file for complete search history.

(56) References Cited

FOREIGN PATENT DOCUMENTS

| JP | 150856 | 6/1989 |
|---|---|---|
| JP | 4073023 | 2/2005 |
| JP | 3116709 | 9/2005 |

OTHER PUBLICATIONS

Henares, et al., "Drop and Sip" Fluid Handling Technique for the Reagent-Release Capillary (RRC)-based Capillary-Assembled Microchip (CAs-CHIP): Sample Delivery Optimization and Reagent Release Behavior in RRC; Analytical Sciences; Jan. 2008; pp. 127-132; vol. 24.

Henares, et a., Multiple Enzyme Linked Immunosorbent Assay System on a Capillary-Assembled Microchip Integrating Valving and Immuno-Reaction Functions; Analytica Chimica Acta; 2007; pp. 173-179; 589.

*Primary Examiner* — N. C. Yang
(74) *Attorney, Agent, or Firm* — Stites & Harbison PLLC; Terry L. Wright

(57) ABSTRACT

A capillary for an immunoassay is provided which comprises an insoluble layer of an oxidase formed on an inner wall surface of said capillary, said oxidase being conjugated to a first antibody, and a layer of a hydrophilic polymer formed on said insoluble layer, said hydrophilic polymer layer containing a second antibody conjugated to a peroxidase, wherein said first and second antibodies are capable of binding to the same antigen.

11 Claims, 2 Drawing Sheets

CAPILLARY FOR IMMUNOASSAY, AND CAPILLARY IMMUNOASSAY METHOD USING SAME

TECHNICAL FIELD

The present invention relates to a capillary for an immunoassay, which is used to sensitively detect a target protein using antigen-antibody reaction in a single step of allowing the capillary to introduce a sample by capillary force, and to a capillary immunoassay method using the capillary.

BACKGROUND ART

Immunoassays are known in which target proteins contained in samples are measured with antibodies capable of specifically binding to the target proteins by using antigen-antibody reaction. For example, sandwich immunoassays are commonly used in which samples containing target proteins are brought into contact with supports such as microtiter plates, magnetic particles, on which primary antibodies capable of binding to the target proteins are immobilized, so as to allow the binding of the target proteins to the primary antibodies; secondary antibodies capable of binding to the same target proteins are then allowed to bind to the target proteins; and labelling substances conjugated to the secondary antibodies are detected.

Immunoassays using as supports microtiter plates, magnetic particles and the like are carried out in a volume of around several hundreds of microliters and therefore use a large amount of antibodies directed to the target proteins. Thus, they may require a large amount of expensive antibodies and also be difficult to measure multiple target proteins. In addition, the immunoassays have other disadvantages: they generally take several hours to react target proteins with the antibodies; they require very laborious operations such as solution exchange, washing and others due to the multistep reaction; and they are not highly sensitive.

A microchannel device has been known which comprises a glass or plastic capillary embedded therein in at least a portion of the channel (Japanese Patent No. 4073023: Patent Literature 1). It is also known that such a capillary for a microchannel device can be used for an immunoreaction.

By using the technologies, capillary immunoassays have been recently developed in which antigen-antibody reactions are carried out in square capillaries having bores of about 100 µm on a side (for example, Henares T. G. et al., Analytica Chimica Acta 589 (2007) p. 173-179: Non-patent Literature 1). These use sandwich immunoassays in which the presence of antigens is detected with primary and secondary antibodies by passing antigen solutions, the enzyme-conjugated secondary antibodies and substrate solutions sequentially through the capillaries to which the primary antibodies are immobilized on the inner wall surfaces.

Such small volume measurement systems made it possible to reduce the amount of antibodies to be required.

In these methods, however, after flowing the antigen solutions and the enzyme-conjugated secondary antibodies through the capillaries, a washing step is required for washing off unbound antigens and secondary antibodies. This makes the capillary immunoassay methods laborious.

CITATION LIST

Patent Literature

Patent Literature 1: Japanese Patent No. 4073023

Non-Patent Literature

Non-patent Literature 1: Henares T. G. et al., Analytica Chimica Acta 589 (2007) p. 173-179

SUMMARY OF INVENTION

Technical Problem

The present invention aims to provide a capillary used for carrying out a simple, single-step immunoassay in a short period of time without a washing step, which is required in the conventional capillary immunoassays, and also a method for the immunoassay.

Solution to Problem

The present invention provides a capillary for an immunoassay comprising:
an insoluble layer of an oxidase formed on an inner wall surface of said capillary, said oxidase being conjugated to a first antibody; and
a layer of a hydrophilic polymer formed on said insoluble layer, said hydrophilic polymer layer containing a second antibody conjugated to a peroxidase,
wherein said first and second antibodies are capable of binding to the same antigen.

The present invention also provides a process for producing the above-mentioned capillary, which comprises the steps of:
activating an inner wall surface of a capillary;
binding an oxidase to said activated inner wall surface;
conjugating a first antibody to said oxidase, thereby forming an insoluble layer; and
forming on said insoluble layer, a layer of a hydrophilic polymer containing a second antibody conjugated to a peroxidase.

The present invention also provides a capillary immunoassay method for detecting a target protein suspected to be present in a sample, which method comprises the step of introducing into the above-mentioned capillary, said sample to which a substrate for said oxidase, a dye convertible to its detectable form by oxidation catalysed by said peroxidase and a hydrogen peroxide-capturing agent have been added.

The present invention further provides a microchannel device comprising a branched or lattice channel formed therein and the above-mentioned capillary embedded in at least a portion of said channel.

Advantageous Effects of Invention

The present capillary allows to rapidly carry out a simple, single-step immunoassay without a washing step, which is required in the conventional capillary immunoassays. In addition, the present method using a small volume reaction system makes it possible to reduce the reaction time and detect the target protein with higher sensitivity.

DESCRIPTION OF EMBODIMENTS

<Capillary for Immunoassay>

Figure 1:
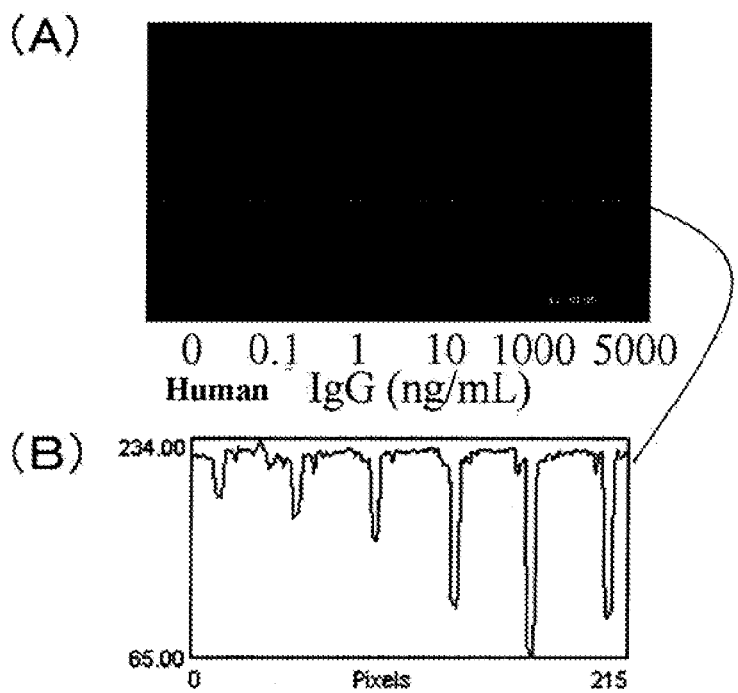
FIG. 1 represents a fluorescent image obtained in Example 1 wherein a target protein was detected with capillaries according to the present invention and fluorescent intensity data from the image.

The capillary for an immunoassay according to the present invention is a capillary used for detecting and measuring a target protein based on antigen-antibody reaction. As used herein, "antigen-antibody reaction" refers to a binding reaction between a protein and an antibody that recognizes and specifically binds to the protein. It should be appreciated by a person skilled in the art that an "antigen", or a target protein, is any protein capable of specifically binding to an antibody and it is not always intended to mean a substance exhibiting immunogenicity by binding to an antibody.

In the present capillary, antigen-antibody reactions are carried out by a "sandwich method" in which the presence of a target protein is detected with two different antibodies capable of specifically binding to the target protein. Thus, the "first antibody" and the "second antibody" as used herein are capable of binding to the same antigen (target protein) at different recognition sites. For convenience, the two different antibodies are referred to as the "first antibody" or the "second antibody" according to whether they are conjugated to the oxidase or the peroxidase, respectively. It should be appreciated by a person skilled in the art that any one of the antibodies may be used as the "first antibody" or the "second antibody" irrelevantly to the positions in the amino acid sequence of the protein.

The target protein, which can be detected and measured with the present capillary, is any protein against which an antibody can be prepared. Target proteins include disease marker proteins, which can be present in samples such as blood, urine, spinal fluid, cell lysates and used as diagnostic indicators, and candidate compounds in the research for useful medicines.

Disease marker proteins include cancer markers (for example, carcinoembryonic antigen (CEA), α-fetoprotein (AFP), human chorionic gonadotrophin (hCG), basic fetoprotein (BFP), squamous cell carcinoma-related antigen (SCC antigen), BCA225, CA15-3, CA19-9, CA50, CA54/61, CA72-4, CA125, CA130, CA602, pancreatic cancer-associated antigen (DUPAN-2), KMO-1, NCC-ST-439, sialyl Lex-i antigen (SLX), cytokeratin 19 fragment (CYFRA), tissue polypeptide antigen (TPA), immunosuppressive acid protein (IAP), prostate-specific antigen (PSA), neuron-specific enolase (NSE), ferritin, elastase 1, p53 antibody, gastrin-releasing peptide precursor (ProGRP), prostatic acid phosphatase (PAP), γ-seminoprotein (γ-Sm), Dpyr, polyamine, BJP, etc.), diabetes markers (for example, insulin, etc.), obesity markers (for example, leptin, adiponectin, etc.), inflammatory markers (for example, C-reactive protein (CRP), etc.), atherosclerotic markers (for example, homocysteine, etc.), renal function markers (for example, cystatin C, etc), HIV markers (p24 antigen), hepatitis markers (HBs antigen, HBs antibody, HBe antigen, HBe antibody) and the like. Immunoglobulins such as IgG, IgA, IgE, IgD and IgM can also be target proteins to be detected and measured, which are known as markers of various diseases.

<Capillary>

The present capillary is preferably constructed of a material transparent to the light generated (fluorescent light, visible light) or the colour developed in immunoassays. Such materials include glass and plastics such as polystyrene, polyethylene, polypropylene, polyethylene terephthalate, poly (methyl methacrylate) (PMMA), poly(methyl acrylate), polydimethylsiloxane (PDMS).

The present capillary can have any shape in the cross section (perpendicular to its longitudinal direction), such as quadrangle and circle. The cross section is preferably quadrangular including square and rectangular, and more preferably square, since such shapes make it possible to detect the light generated or the colour developed in immunoassays more easily.

Where the capillary has a quadrangular cross section, the outer shape of the cross section has preferably 200 µm to 2 mm, and more preferably 200 µm to 1 mm on a side. The bore in the cross section has preferably 50 µm to 1 mm, and more preferably 50 µm to 300 µm on a side.

Such capillaries are commercially available. For example, a glass capillary having a cross section of outer 300 µm×300 µm square and inner 100 µm×100 µm square is commercially available under the tradename Square Flexible Fused Silica Capillary Tubing (Polymicro Technologies).

The length of the capillary can be selected appropriately according to the kinds of target proteins to be measured. Capillaries provided usually with a length of 10 cm to 1 m may be cut into pieces having a desired length after the formation of the insoluble and hydrophilic polymer layers as described below. When used, the present capillary preferably has a length of 0.5 mm to 5 mm, and more preferably 0.5 mm to 2 mm, in view of an appropriate reaction volume.

<Insoluble Layer>

In the present capillary, an insoluble layer of an oxidase conjugated to a first antibody is formed on the inner wall surface.

As used herein, the "insoluble layer" refers to a layer made of oxidase conjugated to the first antibody, which oxidase binds to the inner wall surface in such a manner that the binding is not broken when contacted with water.

The insoluble layer may be formed on at least a part of, preferably on the entire of, the inner wall surface of the present capillary.

The binding between the inner wall surface of the present capillary and the oxidase is by a covalent bond. Methods for forming such a covalent bond are in itself known. For example, an appropriate covalent bond can be formed between the activated surface of a glass or plastic and a functional group of an amino acid of the protein (oxidase). The activation of a glass or plastic includes functionalization with a compound having at least one functional group such as an amino group, a methacryl group, a carboxy group, an isocyanate group, an epoxy group, an aldehyde group or SH group.

The oxidase is any enzyme that oxidizes its substrate by using oxygen as electron acceptor to generate hydrogen peroxide. Such oxidases include glucose oxidase, galactose oxidase, amino acid oxidase, glutamate oxidase, lactate oxidase, pyruvate oxidase, oxalate oxidase, alcohol oxidase, glycerol oxidase, histamine oxidase, urate oxidase, xanthine oxidase, choline oxidase, cholesterol oxidase and the like. The oxidases whose substrates are readily available are preferably used. Preferable are glucose oxidase and amino acid oxidase.

The first antibody is any antibody that is capable of specifically binding to the target protein. The antibody may be monoclonal or polyclonal. It may be of any class such as IgG or IgM. The first antibody may be an antibody fragment retaining the capability of binding to the target protein. Such antibody fragments include Fab fragments, F(ab') fragments, F(ab)2 fragments, sFv fragments and the like.

The first antibody can be derived from any mammals and birds such as human, mouse, rabbit, rat, goat, sheep and chicken. It may be produced by recombinant genetic engineering.

The first antibody can be obtained by any of the methods known in the art according to the target protein. For example, the first antibody may be obtained from a hybridoma prepared by a method which is in itself known. Such hybridomas can be prepared by immunizing an appropriate mammal (for example, mouse, rat) with an antigen (target protein), which has been optionally mixed with an appropriate adjuvant, and fusing antibody-producing cells such as spleen cells, lymph node cells and B lymphocytes from the animal with myeloma cells derived from an appropriate mammal (for example, mouse, rat). Usually, antibody-producing cells and myeloma cells are from the same animal species.

Cell fusion can be carried out by for example the PEG method in which antibody-producing cells and myeloma cells are fused in the presence of a polyethylene glycol in an appropriate medium. After cell fusion, hybridomas are selected in a selection medium such as the HAT medium and screened for the ability to produce antibodies recognizing the target protein by a conventional method (for example, enzyme immunoassay (EIA)). Then, the hybridomas are cloned by a conventional method (for example, limiting dilution) and a hybridoma clone is selected which produces an antibody capable of binding to the target protein. The antibody can be obtained from the hybridoma clone.

The first antibody may be a commercially available antibody according to the target protein.

The first antibody and the oxidase are directly or indirectly conjugated to each other. For example, the first antibody and the oxidase may be conjugated via a pair of substances specifically binding to each other. Such pairs of two binding substances include biotin and streptavidin or avidin, haptens and anti-hapten antibodies, nickel and histidine-tag ((His)6-tag), glutathione and glutathione-S-transferase, and the like. Haptens and anti-hapten antibodies include dinitrophenol (DNP) and an anti-DNP antibody, biotin and an anti-biotin antibody, and the like.

One of the pair of binding substances may be linked to the oxidase, while the other to the first antibody. One of the binding substances to the oxidase or the first antibody can be linked by a method which is in itself known (for example, by forming a covalent bond between a reactive functional group such as a N-hydroxysuccinimidyl (NHS) group and a maleimide group, and an amino (NH2) or mercapto (SH) group of an amino acid; or by expressing a recombinant protein by the use of genetic engineering). The oxidase linked to one of a binding pair is brought into contact with the first antibody linked to the other of the binding pair, thereby conjugating the oxidase to the first antibody.

Preferably, the first antibody is conjugated to the oxidase in such a manner that the antigen recognition site is not hindered. In order to allow the formation of such a conjugation, one of the two binding substances is linked preferably to a portion other than the antigen recognition site, preferably the Fc portion of the first antibody.

Alternatively, the first antibody and the oxidase can be conjugated through a first antibody-directed substance, instead of the binding substances. The first antibody-directed substance may be a substance capable of binding to a portion other than the antigen recognition site, preferably the Fc portion, of the first antibody, including protein A and protein G. Protein A is preferred due to a lower level of non-specific adsorption.

The linkage between the first antibody-directed substance and the oxidase can be formed by a method which is in itself known. Where the first antibody-directed substance is a protein for example, it is possible to link the first antibody-directed substance to the oxidase by introducing a reactive functional group such as an NHS or maleimide group into one of the first antibody-directed substance and the oxidase and forming a covalent linkage between the functional group and an amino or mercapto group of an amino acid in the other protein. It is also possible to link the first antibody-directed substance to the oxidase by forming a covalent linkage between an aldehyde group introduced into the oxidase and an amino or SH group of the first antibody-directed substance.

<Hydrophilic Polymer Layer>

In the present capillary, a layer of a hydrophilic polymer containing a second antibody conjugated to a peroxidase is formed on the insoluble layer.

The hydrophilic polymer is any polymer capable of being solubilized when contacted with water. Such hydrophilic polymers include polyethylene glycols, dextrans, hydroxyethyl cellulose and the like.

Polyethylene glycols of any molecular weight may be used, including those with a molecular weight of 200 to 4,000,000. In particular, it is preferable if they have a molecular weight of 2,000 to 100,000, more preferably 6,000 to 50,000 in view of easy handling.

The hydrophilic polymer layer is preferably constructed of a buffer solution containing the hydrophilic polymer. The buffer solution is any buffer solution capable of maintaining a pH that does not affect the peroxidase and the second antibody contained in the hydrophilic polymer layer. The buffer solution may be a buffer solution capable of maintaining a pH of 6 to 9. As such a buffer solution, a phosphate buffered saline (PBS), a Tris-HCl buffer solution, an HEPES buffer solution, a borate buffer solution or the like can be used.

In the case of the hydrophilic polymer being a polyethylene glycol, the concentration of the polyethylene glycol in the buffer solution is in a range where the buffer solution has a sufficient viscosity to remain on the insoluble layer. The kinematic viscosity is preferably 1,000 to 2,000 cSt. In order to provide a buffer solution having such a kinematic viscosity, the concentration of the polyethylene glycol in the buffer solution is preferably 100 to 300 g/L, although it varies depending on the molecular weight of the polyethylene glycol.

The peroxidase, which is conjugated to the second antibody and contained in the hydrophilic polymer layer, is a peroxidase derived from a plant, animal or microbe, or a recombinant peroxidase obtained according to a genetic engineering technique. Horseradish peroxidase (HRP) is preferably used because it is widely used in the biochemical field.

The second antibody, which is conjugated to the peroxidase and contained in the hydrophilic polymer layer, is such an antibody that specifically binds to the same target protein as the first antibody but at a different site. Other properties and preparation method of the second antibody are as described for the first antibody.

The conjugation between the peroxidase and the second antibody can be performed by a method which is in itself known. For example, it is possible to conjugate the second antibody to the peroxidase by modifying the peroxidase with a reactive functional group such as an NHS or maleimido group and reacting the functional group with an amino (NH2) or mercapto (SH) group of an amino acid in the second antibody.

Especially, many antibodies conjugated with HRP are commercially available. Such commercially available HRP-labelled antibodies can be used as the second antibody in the present invention.

<Process for Preparing Capillary for Immunoassay>

The present capillary can be prepared by a method which is in itself known. Specifically, the capillary for an immunoassay can be obtained by a method comprising the steps of: (1) activating an inner wall surface of a capillary; (2) binding an oxidase to said activated inner wall surface; (3) conjugating a first antibody to said oxidase, thereby forming an insoluble layer; and (4) forming on said insoluble layer, a layer of a hydrophilic polymer containing a second antibody conjugated to a peroxidase. The method may comprise between the successive steps, a step(s) of washing with an appropriate buffer solution.

(1) Activation of Inner Wall Surface of Capillary

The inner wall surface of the capillary can be activated with a compound having a functional group as described above according to a method which is in itself known.

Where the capillary's inner wall surface is activated with an aldehyde group, the surface activation can be carried out by treating the inner wall surface with a silane-coupling agent, drying, and introducing an amino group to the surface, followed by reacting the amino group with an aldehyde-containing compound such as glutaraldehyde so as to introduce the aldehyde group to the surface.

Silane-coupling agents include amino alkoxysilanes such as γ-aminopropyltrimethoxysilane and 3-aminopropyltriethoxysilane; epoxysilanes such as 3-glycidoxypropyltrimethoxysilane; methacryl silanes such as 3-(trimethoxysilyl)propyl methacrylate; chloroalkyl silanes such as (chloromethyl)triethoxysilane.

It is possible to improve the efficiency of binding of the oxidase to the capillary's inner wall surface in the subsequent step by further treating the aldehyde group-activated surface with polyethyleneimine and an aldehyde-containing compound.

Where the capillary's inner wall surface is activated with an epoxy group, the surface activation can be carried out by treating the surface with a silane-coupling agent, drying, and introducing the epoxy group.

(2) Binding of Oxidase to Activated Inner Wall Surface

The binding of the oxidase to the capillary's inner wall surface via a covalent bond is performed by introducing an aqueous solution containing the oxidase into the capillary subjected to the activation treatment in step (1) and reacting for an appropriate period of time.

The aqueous solution containing the oxidase preferably has a pH of 8 to 9. In order to obtain such a pH, an appropriate buffer can be used.

The concentration of the oxidase in the aqueous solution is preferably 3 to 5 mg/mL.

It is preferable if the aqueous solution containing the oxidase is reacted for around 30 minutes to 2 hours at a temperature of 25° C. to 40° C.

(3) Conjugation of First Antibody to Oxidase

The insoluble layer can be formed by introducing an aqueous solution containing the first antibody to the capillary obtained in the step (2) and reacting for an appropriate period of time so as to conjugate the first antibody to the oxidase. If the above-mentioned first antibody-directed substance is used, the conjugation of the first antibody to the oxidase is performed by introducing into the capillary a modifying agent, which allows for linkage of the first antibody-directed substance to the oxidase, and then the first antibody-directed substance, followed by the first antibody.

The aqueous solution containing the first antibody preferably has a pH of 7 to 7.4. In order to obtain such a pH, an appropriate buffer can be used.

The concentration of the first antibody in the aqueous solution is preferably 10 to 100 μg/mL.

Where protein A is used as the first antibody-directed substance, it is preferable that protein A is allowed to bind to the oxidase and then the aqueous solution containing the first antibody is reacted for around 30 minutes to 2 hours at a temperature of 25° C. to 40° C.

In order to prevent non-specific protein adsorption, a coat may be formed by introducing bovine serum albumin (BSA), skim milk, or the like after the first antibody.

(4) Formation of Hydrophilic Polymer Layer

Following step (3), the hydrophilic polymer layer can be formed on the insoluble layer, which is formed on the capillary's inner wall surface, by continuously introducing into the capillary the hydrophilic polymer in which the second antibody conjugated to the peroxidase is dissolved.

The hydrophilic polymer may be dissolved in an appropriate buffer as described above so as to obtain the above-mentioned appropriate viscosity.

The concentration of the second antibody conjugated to the peroxidase in the hydrophilic polymer is preferably 10 to 100 μg/mL.

The rate of the continuous introduction of the hydrophilic polymer into the capillary is preferably several tens of microliters per minute since the hydrophilic polymer layer can be formed better.

The capillary thus prepared can be stored at a cool temperature (−20° C. to 10° C.) until use.

<Capillary Immunoassay Method>

The present invention also provides a capillary immunoassay method comprising detecting a target protein suspected to be present in a sample using the above-described capillary for an immunoassay.

The sample is any sample in which the target protein is suspected to be present. Such samples include fluids derived from biological samples such as blood, urine and spinal fluid, cell lysates, aqueous solutions and the like.

The present immunoassay method can be carried out by introducing a sample to the above-described capillary. The introduction of the sample can be effected through capillary action by contacting the sample with an end (inlet end) of the capillary.

The sample introduced into the capillary may generally be 0.05 to 0.1 μl, although the amount depends on the size of the capillary.

For reaction, the sample introduced is preferably retained in the capillary for 5 minutes to 1 hour, more preferably 10 minutes to 30 minutes, at a temperature of 20° C. to 40° C., more preferably 25° C. to 38° C.

To the sample, added are a substrate for the oxidase, a dye convertible to its detectable form by oxidation catalysed by the peroxidase and a hydrogen peroxide-capturing agent.

The oxidase substrate can be selected appropriately according to the oxidase used.

In general, it is preferable that the oxidase substrate is added to the sample so as to obtain a concentration of 10 to 50 mM, although it depends on the kind of the substrate.

The dye convertible to its detectable form by peroxidase-catalysed oxidation may be any of fluorescence dyes, chromogenic dyes and chemiluminescence dyes. The chromogenic dyes include 3,3'-diaminobenzidine (DAB), 3,3',5,5'- tetramethylbenzidine (TMB), 3-amino-9-ethylcarbazole (AEC), Methyl Green, combinations of an N-ethyl-m-toluidine derivative (for example, an N-hydroxysulfopropyl derivative (TOOS)) and 4-aminoantipyrine (4-AA), and the like. The fluorescence dyes include 10-acetyl-3,7-dihydroxy phenoxazine (Amplex Red), p-hydroxyphenylacetate, thiamine and the like. The chemiluminescence dyes include luminol and the like.

In general, it is preferable that the dye convertible to its detectable form by peroxidase-catalysed oxidation is added to the sample so as to obtain a concentration of 0.1 to 1 mM, although it depends on the kind of the dye.

The hydrogen peroxide-capturing agent is any of substances capable of reacting with hydrogen peroxide to degrade it to water, including ascorbic acid, glutathione, histidine, uric acid, transition metals (such as $Fe^{2+}$, $Ti^{3+}$, $Co^{2+}$), sodium hypochlorite (NaOCl).

It is preferable that the hydrogen peroxide-capturing agent is added to the sample so as to obtain a concentration of 0.1 to 100 mM, and more preferably 1 to 10 mM, although it depends on the kind of the agent.

The principle of the present capillary immunoassay method is now described. When a sample is introduced into the capillary and if a target protein is present in a sample, the first antibody and the second antibody form a complex via the target protein in the vicinity of the capillary's inner wall surface. Then, the oxidase substrate that has been added to the sample is oxidized by the oxidase conjugated to the first antibody to generate hydrogen peroxide. This hydrogen peroxide, together with the peroxidase conjugated to the second antibody that is complexed with the first antibody via the target protein, converts the dye that has been added to the sample to its detectable form. Thus, the presence of the antigen can be detected in a single step.

If the target protein is not present, on the other hand, the first antibody and the second antibody cannot form a complex so that they are far from each other in the capillary. The oxidase on the inner wall surface generates hydrogen peroxide from the substrate added to the sample. However, the hydrogen peroxide cannot be used by the peroxidase conjugated to the second antibody, which is far from the oxidase conjugated to the first antibody. It is captured and degraded to water by the hydrogen peroxide-capturing agent, which has been added to the sample. Thus, the dye added to the sample cannot be converted to its detectable form.

When converted to its detectable form, the dye can be detected from outside the capillary with a detector according to the type of the dye used. Where the dye is a fluorescence dye, the detector may be a fluorescent microscope with an appropriate excitation light source, a fluorometer, a CCD camera, a photodiode, a photomultiplier or the like. Where the dye is a chromogenic dye, the detector may be a spectrophotometer, a CCD camera, a photodiode, a photomultiplier or the like. Where the dye is a chemiluminescence dye, the detector may be a CCD camera, a photodiode, a photomultiplier or the like.

The detector is preferably connected to an analyzer quantifying the signal from the dye by a software program.

The present capillary immunoassay method is based on two different reactions: antigen-antibody reaction and enzyme reaction. Antigen-antibody reactions are reactions between two proteins having high molecular weights, and therefore generally proceed very slowly (usually it takes several hours). In the present capillary immunoassay method, however, the antigen-antibody reactions proceed more rapidly (it takes about 10 to 20 minutes) because they occur in a capillary having a very small volume (usually several tens to several hundreds of nano liters), thereby shortening the distance that the molecules must diffuse.

On the other hand, enzyme reactions generally proceed very rapidly (usually it takes several tens of seconds to several minutes). In the present method, however, the enzyme reaction proceeds more slowly (it takes about 10 to 20 minutes) because of the hydrogen peroxide-capturing agent added to the sample in an appropriate amount.

According to the present method, therefore, it is possible to limit the rates of the two types of reactions to a preferable range. Consequently, the present method makes it possible to detect a target protein in a concentration of as low as about 1 ng/ml, in a single step of allowing the capillary to absorb a small amount of a sample solution by capillary force, and in a shorter reaction time than the conventional immunoassay methods.

<Microchannel Device Comprising Capillary for an Immunoassay>

The present invention further provides a microchannel device comprising a branched or lattice channel formed therein and the capillary according to claim 1 embedded in at least a portion of said channel.

The shape of the channels as well as the materials and production method of the microchannel device are as described in Japanese Patent Kokai (Unexamined) Publication No. 2005-140681.

Figure 3:
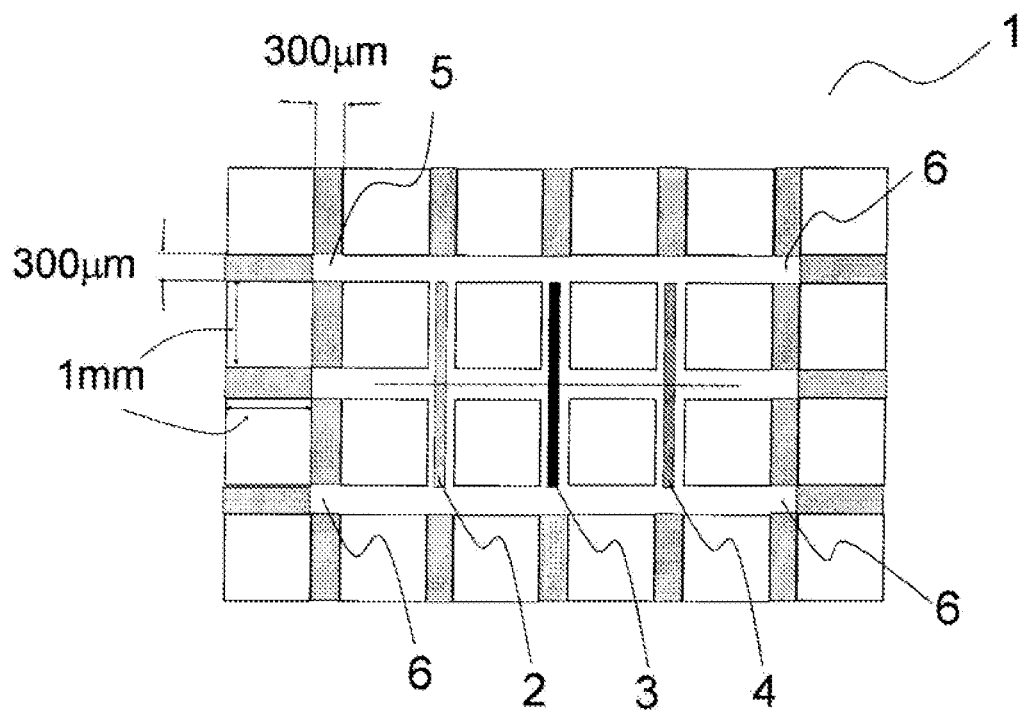
FIG. 3 is a schematic diagram of one embodiment of a microchannel device comprising the capillaries according to the present invention.

One preferred embodiment of the present microchannel device is illustrated in FIG. 3. FIG. 3 represents a microchannel device 1 provided with channels having a width of 300 μm. In portions of this microchannel device are embedded a capillary for an immunoassay 2 comprising first and second antibodies capable of binding to AFP, a capillary for an immunoassay 3 comprising first and second antibodies capable of binding to CEA and a capillary for an immunoassay 4 comprising first and second antibodies capable of binding to hCG. A sample is fed dropwise to the sample feed port 5 of the microchannel device. The sample is drawn from the sample draw port 6, thereby introducing the sample into each capillary by capillary force. AFP, CEA and hCG can be detected in a single step by measuring fluorescence intensities at certain points (as indicated by the dashed line, for example) of each of the capillaries.

EXAMPLES

Preparation Example 1

Preparation of Capillary for Immunoassay

A. Surface Modification of Square Capillary
1. Into a 300 μm square capillary having a 100 μm square bore (Polymicro technologies; WWP100375) was introduced 1 N NaOH. It was then left to stand for 30 minutes.
2. The capillary was washed with a sufficient amount of pure water passed therethrough and then water was pushed out with acetone introduced.
3. The capillary was dried in an oven at 70° C. for 30 minutes.
4. Into the capillary was introduced a 30% (v/v) solution of 3-aminopropyltriethoxysilane (APTES) in acetone. It was then left to stand for 40 minutes at room temperature.
5. After washing with acetone, the capillary was dried in an oven at 70° C. for 60 minutes.
6. Into the capillary was introduced a 2.5% (v/v) glutaraldehyde aqueous solution. It was allowed to react for 40 minutes at room temperature.
7. The capillary was washed with pure water.

8. Into the capillary was introduced a 5% (v/v) polyethyleneimine aqueous solution (in a phosphate buffered saline, pH 9). It was allowed to react for 40 minutes at room temperature to immobilize polyethyleneimine having multiple amino groups on the capillary's inner wall surface.
9. The capillary was washed with a phosphate buffered saline, pH 9.
10. Into the capillary was introduced a 2.5% (v/v) glutaraldehyde aqueous solution It was allowed to react for 40 minutes at room temperature.
11. The capillary was washed with a phosphate buffered saline, pH 9.

B. Formation of Insoluble Layer of Oxidase Conjugated to First Antibody on Capillary's Inner Wall Surface 1. Into the capillary whose inner wall had been modified with glutaraldehyde as described in (A) was introduced an aqueous solution (in a phosphate buffered saline, pH 9) of glucose oxidase (5 mg/mL; Sigma G7141). It was allowed to react for 40 minutes at room temperature.
2. The capillary was washed with a phosphate buffered saline, pH 9.
3. Into the capillary was introduced a 2.5% (v/v) glutaraldehyde aqueous solution. It was allowed to react for 40 minutes at room temperature.
4. The capillary was washed with a phosphate buffered saline, pH 9.
5. To the capillary was added an aqueous solution (in a phosphate buffered saline, pH 9) of Protein A (0.5 mg/mL; Sigma P6031). It was allowed to react for 40 minutes at room temperature to conjugate Protein A to the glucose oxidase modified with aldehyde groups.
6. The capillary was washed with pure water.
7. Into the capillary was introduced a 0.1 M NaBH4 aqueous solution. It was allowed to react for 40 minutes at room temperature.
8. The capillary was washed with pure water and then with a Tris-HCl buffer, pH 7.4.
9. Into the capillary was introduced anti-human IgG (Funakoshi, E80-104 Human ELISA quantification kit), as the first antibody, diluted to 1/100 in a Tris-HCl buffer, pH 7.4. It was allowed to react for 40 minutes at room temperature to attach the first antibody to Protein A.
10. The capillary was washed with a Tris buffer, pH 7.4.
11. Into the capillary was introduced a 1% solution of bovine serum albumin (BSA) in a Tris buffer, pH 7.4. It was then left to stand for more than 2 hours at room temperature to form on the capillary's inner surface, a coating for the prevention of non-specific adsorption.
12. The capillary was washed with a Tris buffer, pH 7.4.

C. Formation of Hydrophilic Polymer Layer Comprising Second Antibody Conjugated to Peroxidase 1. Horseradish peroxidase (HRP)-labelled anti-human IgG (Funakoshi, E80-104 Human ELISA quantification kit), as the second antibody, was diluted to 1/100 in a Tris-HCl buffer, pH 7.4, in which a polyethylene glycol (PEG; MW=20000) had been dissolved at 300 mg/mL. This solution was fed to the capillary at the rate of 20 µL/min and immediately thereafter drawn at the rate of 30 µL/min, so that a polyethylene glycol layer containing the second antibody conjugated to the peroxidase is formed on the insoluble layer of the glucose oxidase conjugated to the first antibody.
2. The capillary for an immunoassay can be stored at −10° C., if it is not used just after the preparation.

Example 1

Sample solutions were prepared by dissolving the following ingredients in a Tris-HCl buffer, pH 9:

Dye convertible to its detectable form by the peroxidase-catalysed oxidation: 0.8 mM Amplex Red (Invitrogen, A36006);
Oxidase substrate: 28 mM glucose;
Hydrogen peroxide-capturing agent: 10 mM ascorbic acid; and
Target protein: human IgG (0, 0.1, 1, 10, 1,000 and 5,000 ng/mL; Funakoshi, E80-104 Human ELISA quantification kit).

The sample solutions were brought into contact with 5 mm capillaries made by cutting the capillary prepared as Preparation Example 1. 0.05 µl of the sample solutions were introduced into the capillaries by capillary force. The capillaries containing the sample solutions were left to stand for 30 minutes at room temperature.

The capillaries, into which the target protein was introduced for reaction, were placed under a fluorescence microscope (KEYENCE VB7000) equipped with a mercury lamp (excitation filter wavelength: 540/25 nm, absorbance filter wavelength: 572 nm) and a fluorescent image was acquired.

The digital image was then analyzed to quantify fluorescence signals by using software programs including Image-J (a free software program published by the National Institute of Health (NIH): URL http://rsbweb.nih.gov/ij/).

The fluorescent image is shown in FIG. 1 (A). The fluorescence signals are shown in FIG. 1 (B), which were measured at the level of about 2.5 mm from the inlet ends of the capillaries (indicated by the dashed line).

Figure 2:
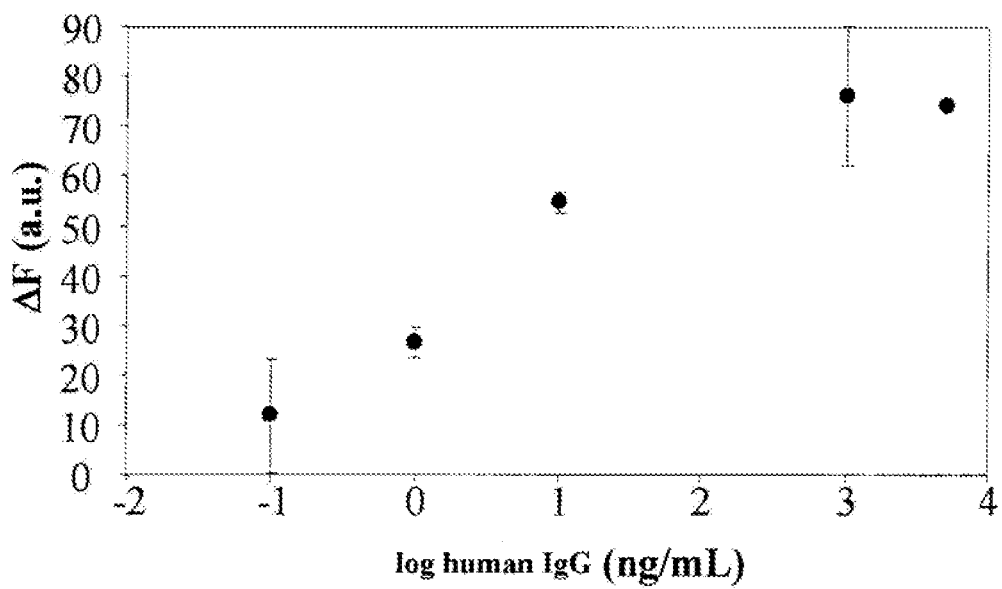
FIG. 2 is a plot graph of the fluorescence intensities vs. the concentrations of the target protein.

FIG. 2 represents a plot graph of the fluorescence intensities ($\Delta F$) at the respective antigen concentrations, which were obtained by using the signals at a concentration of 0 (zero) as background signals, against the concentrations of the target protein in a logarithmic scale.

As seen from these results, the fluorescence intensity is in approximately proportional to the concentration of the target protein in immunoassay using the present capillary.

Thus, it is now confirmed that the immunoassay using the present capillary can detect and quantify a target protein in a small amount of sample solution, simply in a single step without a washing step and in a relatively shorter period of time.

Preparation Example 2

Preparation of Capillary for HIV Antigen Immunoassay

A. Surface Modification of Square Capillary

The inner surface of a square capillary was modified as described in Production Example 1 (A).

B. Formation of Insoluble Layer of Oxidase Conjugated to First Antibody on Capillary' Inner Surface 1. Into the capillary whose inner surface had been modified with glutaraldehyde as described in (A) was introduced an aqueous solution (in a phosphate buffered saline, pH 9) of glucose oxidase (5 mg/mL; Sigma G7141). It was allowed to react for 40 minutes at room temperature.
2. The capillary was washed with a phosphate buffered saline, pH 9.
3. Into the capillary was introduced a 2.5% (v/v) glutaraldehyde aqueous solution. It was allowed to react for 40 minutes at room temperature.
4. The capillary was washed with a phosphate buffered saline, pH 9.
5. To the capillary was added an aqueous solution (in a phosphate buffered saline, pH 9) of anti-HIV-1 (p24) antibody (0.5 mg/mL; Anogen MO-140002D2). It was allowed to react for 40 minutes at room temperature to conjugate the anti-HIV-1 (p24) antibody to the glucose oxidase modified with an aldehyde group.

6. The capillary was washed with pure water.
7. Into the capillary was introduced a 0.1 M NaBH4 aqueous solution. It was allowed to react for 40 minutes at room temperature.
8. The capillary was washed with a Tris buffer, pH 7.4.
9. Into the capillary was introduced a 1% solution of bovine serum albumin (BSA) in a Tris buffer, pH 7.4. It was then left to stand for more than 2 hours at room temperature to form on the capillary's inner surface, a coating for the prevention of non-specific adsorption.
10. The capillary was washed with a Tris buffer, pH 7.4.

C. Formation of Hydrophilic Polymer Layer Comprising Second Antibody Conjugated to Peroxidase
1. Horseradish peroxidase (HRP)-labelled anti-HIV-1 (p24) antibody (Anogen MO-140002T2HRP), as the second antibody, was diluted to 1/100 in a Tris-HCl buffer, pH 7.4, in which a polyethylene glycol (PEG; MW=20000) had been dissolved at 300 mg/mL. This solution was introduced into the capillary at the rate of 20 μL/min and immediately thereafter drawn at the rate of 30 μL/min, so that a polyethylene glycol layer containing the second antibody conjugated to peroxidase is formed on the insoluble layer of glucose oxidase conjugated to the first antibody.
2. This capillary for an immunoassay can be stored at −10° C., if it is not used just after the preparation.

Example 2

Sample solutions were prepared by dissolving the following ingredients in a Tris-HCl buffer, pH 9:
Dye convertible to its detectable form by the peroxidase-catalysed oxidation: 0.8 mM
Amplex Red (Invitrogen, A36006);
Oxidase substrate: 28 mM glucose;
Hydrogen peroxide-capturing agent: 10 mM ascorbic acid; and
Target protein: HIV-1 p24 Antigen (0, 0.1, 1, 10, 100 and 1,000 ng/mL; Biodesign International, R18301).

The sample solutions were brought into contact with 5 mm capillaries made by cutting the capillary prepared as Preparation Example 2. 0.05 μl of the sample solutions were introduced into the capillaries by capillary force. The capillaries containing the sample solutions were left to stand for 30 minutes at room temperature.

The capillaries, into which the target protein was introduced for reaction, were placed under a fluorescence microscope (KEYENCE VB7000) equipped with a mercury lamp (excitation filter wavelength: 540/25 nm, absorbance filter wavelength: 572 nm) and a fluorescent image was acquired.

The digital image was then analyzed to quantify fluorescence signals by using software programs including Image-J (a free software program published by the National Institute of Health (NIH): URL http://rsbweb.nih.gov/ij/).

Figure 4:
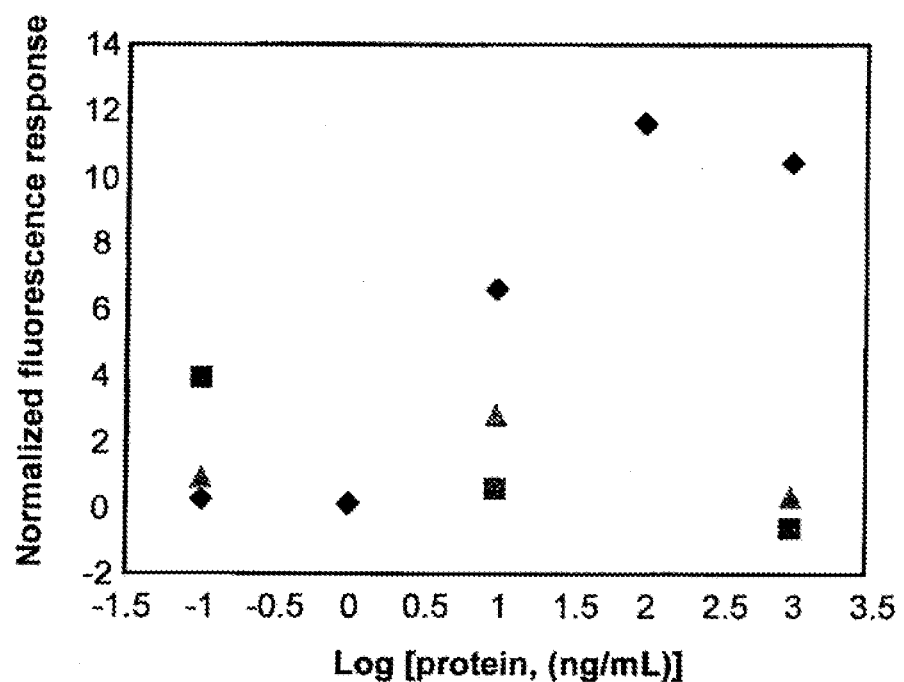
FIG. 4 is a plot graph of fluorescence intensities vs. the concentrations of the target protein HIV-1 (p-24) antigen, which was detected with the capillaries according to the present invention in Example 2.

FIG. 4 represents a plot graph of the fluorescence intensities (ΔF) at the respective antigen concentrations, which were obtained by using the signals at a concentration of 0 (zero) as background signals, against the concentrations of the target protein in a logarithmic scale. FIG. 4 also shows the results obtained from the capillaries into which human IgG (■) or rabbit IgG (▲) was introduced, instead of HIV-1 antigen (♦) as a target protein, in order to measure non-specific responses.

As seen from these results, the fluorescence intensity is in approximately proportional to the concentration of the HIV antigen in immunoassay using the present capillary. It is also found that the present capillary can specifically measure an antigen for the antibody immobilized on its bore and does not react in a dose-dependent manner with any antigens not specifically reacting with the antibody.

Thus, it is now confirmed that the immunoassay using the present capillary can detect and quantify an HIV antigen in a small amount of sample solution, simply in a single step without a washing step and in a relatively shorter period of time.

The present application relates to Japanese Patent Application No. 2008-324059 filed on Dec. 19, 2008, whose claims, specification, drawings and abstract are incorporated herein in their entirety by reference.

REFERENCE SIGNS LIST

1 Microchannel device
2, 3, 4 Capillaries according to the present invention
5 Sample feed port
6 Sample draw port

The invention claimed is:

1. A capillary for an immunoassay comprising:
an insoluble layer of an oxidase formed on an inner wall surface of said capillary, said oxidase being conjugated to a first antibody; and
a layer of a hydrophilic polymer formed on said insoluble layer, said hydrophilic polymer layer containing a second antibody conjugated to a peroxidase,
wherein said first and second antibodies are capable of binding to the same antigen.

2. The capillary according to claim 1, wherein said hydrophilic polymer is a polyethylene glycol having a molecular weight of 2,000 to 100,000.

3. The capillary according to claim 1, wherein said oxidase is glucose oxidase and said peroxidase is horseradish peroxidase.

4. The capillary according to claim 1, wherein the cross section of said capillary perpendicular to the longitudinal direction thereof is quadrangular including square and rectangular, and the bore of said capillary has 50 μm to 1 mm in length on a side.

5. A process for preparing the capillary according to claim 1, comprising the steps of:
activating an inner wall surface of a capillary;
binding an oxidase to said activated inner wall surface;
conjugating a first antibody to said oxidase, thereby forming an insoluble layer; and
forming on said insoluble layer, a layer of a hydrophilic polymer containing a second antibody conjugated to a peroxidase.

6. The process according to claim 5, wherein said capillary's inner surface activation is an activation with a compound having at least one functional group selected from an amino group, a methacryl group, a carboxyl group, an isocyanate group, an epoxy group, an aldehyde group and an SH group.

7. A capillary immunoassay method for detecting a target protein suspected to be present in a sample, the method comprising the step of introducing into the capillary according to claim 1, said sample to which a substrate for said oxidase, a dye convertible to its detectable form by oxidation catalysed by said peroxidase and a hydrogen peroxide-capturing agent have been added.

8. The capillary immunoassay method according to claim 7, wherein said hydrogen peroxide-capturing agent is selected from ascorbic acid, glutathione, histidine, uric acid, transition metal ions and sodium hypochlorite (NaOCl).

9. The capillary immunoassay method according to claim 7, wherein said target protein is a disease marker selected from cancer markers, diabetes markers, obesity markers, inflammatory markers, atherosclerotic markers, renal function markers, HIV markers and hepatitis markers.

10. The capillary immunoassay method according to claim 7, wherein said substrate, said dye and said hydrogen peroxide-capturing agent are added to said sample so as to obtain respective concentrations of 10 to 50 mM, 0.1 to 1 mM and 0.1 to 100 mM.

11. A microchannel device comprising a branched or lattice channel formed therein and the capillary according to claim 1 embedded in at least a portion of said channel.

\* \* \* \* \*